(12) United States Patent
Richter et al.

(10) Patent No.: US 10,251,658 B2
(45) Date of Patent: Apr. 9, 2019

(54) DEVICE FOR RECANALIZATION OF VESSEL OCCLUSIONS USING GUIDE WIRE AND METHOD OF USE

(71) Applicant: MEDINOL LTD., Tel Aviv (IL)

(72) Inventors: Jacob Richter, Arsuf (IL); Amir Pansky, Atlit (IL); Gal Demer, Tel Aviv (IL)

(73) Assignee: Medinol Ltd., Tel Aviv (IL)

( * ) Notice: Subject to any disclaimer, the term of this patent is extended or adjusted under 35 U.S.C. 154(b) by 145 days.

(21) Appl. No.: 15/413,584

(22) Filed: Jan. 24, 2017

(65) Prior Publication Data

US 2017/0189042 A1    Jul. 6, 2017

Related U.S. Application Data

(63) Continuation of application No. 13/022,731, filed on Feb. 8, 2011, now Pat. No. 9,585,679.

(Continued)

(51) Int. Cl.
*A61B 17/22*     (2006.01)
*A61M 25/09*    (2006.01)

(52) U.S. Cl.
CPC .... *A61B 17/22012* (2013.01); *A61B 17/2202* (2013.01); *A61M 25/09* (2013.01);
(Continued)

(58) Field of Classification Search
CPC ...... A61B 17/2202; A61B 2017/22044; A61B 2017/22049; A61B 2017/22094; A61M 25/09; A61M 2025/09125; Y10T 29/49826
See application file for complete search history.

(56) References Cited

U.S. PATENT DOCUMENTS

| 5,405,380 A | 4/1995 | Gianotti et al. |
| 6,007,514 A | 12/1999 | Nita |

(Continued)

FOREIGN PATENT DOCUMENTS

| JP | 2837078 | 12/1998 |
| JP | 11-299896 | 11/1999 |

(Continued)

OTHER PUBLICATIONS

International Search Report and Written Opinion from related PCT Application No. PCT/IB2011/000384 dated Jul. 14, 2011, 16 pages.

(Continued)

*Primary Examiner* — Jocelin C Tanner
(74) *Attorney, Agent, or Firm* — Cadwalader, Wickersham & Taft LLP

(57) ABSTRACT

An attachment mechanism and method for attaching or coupling a guide wire to a catheter for re-canalization or opening a passage through an occlusion in a blood vessel is provided. The attachment mechanism generates friction forces against the guide wire to couple the guide wire to a catheter, which design permits a greater force to be used on the guide wire during a re-canalization procedure. The invention also encompasses use of the attachment mechanism in conjunction with active catheters, which have vibration-generating means to oscillate the distal end of the catheter or a component in the distal end of the catheter, to add vibration motion, preferably axial vibration motion, to the increased force that may be applied to the guide wire for purposes of penetrating an occlusion. The methods of the invention relate to methods of attaching the guide wire to the catheter and methods of treating a vessel having a partial or total occlusion.

14 Claims, 4 Drawing Sheets

Related U.S. Application Data

(60) Provisional application No. 61/302,679, filed on Feb. 9, 2010.

(52) U.S. Cl.
CPC ............... *A61B 2017/22044* (2013.01); *A61B 2017/22049* (2013.01); *A61B 2017/22094* (2013.01); *A61M 2025/09125* (2013.01); *Y10T 29/49826* (2015.01)

(56) References Cited

U.S. PATENT DOCUMENTS

| 6,113,579 | A  | 9/2000  | Eidenschink et al. |
| 6,348,040 | B1 | 2/2002  | Stalker et al. |
| 2008/0294037 | A1 | 11/2008 | Richter |
| 2009/0105653 | A1 | 4/2009  | Spenser et al. |
| 2009/0292296 | A1 | 11/2009 | Pansky et al. |
| 2011/0196397 | A1 | 8/2011  | Frantz et al. |

FOREIGN PATENT DOCUMENTS

| JP | 2009-537211 | 10/2009 |
| SU | 1560125 | 4/1990 |
| WO | WO 91/010403 | 7/1991 |
| WO | WO 00/00104 A1 | 1/2000 |
| WO | WO 01/58360 A2 | 8/2001 |
| WO | WO 2007/132464 A1 | 11/2007 |
| WO | WO 2008/065643 A1 | 6/2008 |
| WO | WO 2009/053839 | 4/2009 |

OTHER PUBLICATIONS

Office Actions and response of related U.S. Appl. No. 13/022,731, now U.S. Pat. No. 9,585,679: Notice of Allowance dated Oct. 24, 2016; Amendment and Response to Non Final Rejection dated Sep. 22, 2016; Non Final Rejection dated Jun. 22, 2016; Amendment and Response to Final Rejection with Request for Continued Examination (RCE) and Extension of Time dated Oct. 8, 2015; Final Rejection dated Jun. 10, 2015; Amendment and Response to Non-Final Rejection with Extension of Time dated Apr. 21, 2015; Non-Final Rejection dated Nov. 26, 2014; Supplemental Response dated Nov. 15, 2013; Amendment and Response to Final Rejection with Request for Continued Examination (RCE) dated Sep. 18, 2013; Applicant Initiated Interview Summary dated Aug. 22, 2013; Final Rejection dated Jun. 19, 2013; Amendment and Response to Non-Final Rejection with Extension of Time dated Apr. 11, 2013; Non-Final Rejection dated Dec. 14, 2012; Response to Election/Restriction Requirement dated Aug. 31, 2012; Requirement for Restriction/Election dated Aug. 6, 2012; Response to Pre-Exam Formalities Notice dated Feb. 23, 2011; and Notice of Omitted Items dated Feb. 22, 2011.

Office Actions and response of related U.S. Appl. No. 14/081,127, now U.S. Pat. No. 9,615,843: Notice of Allowance and Applicant Initiated Interview Summary dated Dec. 22, 2016; Applicant Initiated Interview Summary dated Dec. 13, 2016; Advisory Action and After Final Consideration Program Decision dated Nov. 28, 2016; Response to Final Rejection and After Final Consideration Program Requested with Extension of Time dated Nov. 15, 2016; Final Rejection dated Jul. 15, 2016; Amendment and Response to Non-Final Rejection dated Jun. 20, 2016; and Non-Final Rejection dated Mar. 18, 2016.

DEVICE FOR RECANALIZATION OF VESSEL OCCLUSIONS USING GUIDE WIRE AND METHOD OF USE

This application is a continuation of U.S. patent application Ser. No. 13/022,731 filed Feb. 8, 2011 and claims the benefit of priority of U.S. Provisional Application Ser. No. 61/302,679, filed Feb. 9, 2010, all of which are incorporated herein by reference in their entirety.

FIELD OF THE INVENTION

The invention is directed to the use of a guide wire within a support catheter or active catheter for penetrating a total occlusion of a blood vessel during percutaneous coronary intervention ("PCI") using a guide wire. In particular, the apparatus provides a mechanism for enhancing the axial force that may be applied to the guide wire, or for transferring vibration energy to a guide wire at the distal tip of the PCI device, to use the distal end of the guide wire to penetrate the occlusion.

BACKGROUND OF THE INVENTION

Medical science has long sought effective treatments for disease conditions involving stenosis (narrowing or obstruction) of the lumen of an artery. This condition, known generally as an occlusion, occurs in patients suffering from atherosclerosis, which is characterized by an accumulation of fibrous, fatty or calcified tissue in the arteries, otherwise known as atheromata or plaques. An occlusion may be partial or total; it may be soft and pliable or hard and calcified. Occlusions can arise at a great variety of sites in the arterial system including the aorta, the coronary and carotid arteries, and peripheral arteries. An occlusion can result in hypertension, ischemia, angina, myocardial infarction, stroke and even death.

Minimally invasive procedures are the preferred treatment of arterial occlusions. In these procedures, a catheter—a long, highly flexible tubular device—is introduced into a major artery through a small arterial puncture made in the groin, upper arm, upper leg, or neck. The catheter is advanced and steered into the site of the stenosis. A great variety of devices have been developed for treating the stenosed artery, and these devices are placed at the distal end of the catheter and delivered thereby. Example procedures include percutaneous transluminal coronary angioplasty (PTCA), directional coronary atherectomy (DCA), and stenting.

In a total occlusion, a passageway must first be opened through the occlusion to allow the balloon/stent catheter to be placed in the target stenosed segment of the vessel. As occlusion morphology is complicated and varies from patient to patient, common methods and devices for opening these occlusions have had limited success and require long procedures with potentially adverse effects on the patient. Such adverse effects include perforation of blood vessel wall, high radiation dose or damage to kidneys due to extensive use of angiographic contrast material.

Stenoses, or occlusions, are made of a variety of materials—from softer fatty substances such as cholesterol, to tougher fibrous material, to hard calcified material. Generally the ends of the occlusion—the proximal and distal caps—comprise the harder calcified material. The harder materials are more difficult to penetrate, requiring a significant amount of energy, the softer materials require less energy. Therefore, opening an occlusion requires transfer of relatively extensive energy to the distal end of a catheter or guide wire, especially when calcification is present.

Some available methods for opening total occlusions are radio-frequency ablative energy (as used in the system sold by Intralumenal Therapeutics as Safecross™), vibrational energy of about 20 kHz and small amplitudes (as used in the system sold by FlowCardia Inc. as Crosser™), dedicated stiff guide wire which pushes a passage through the occlusion (as developed by Asahi Intec Co. and distributed as Confianza 9 g/Conquest and Miracle 12 g guide wires) and mechanical vibration elements working at high frequency (FlowCardia Inc.'s Crosser™). The latter means for opening occlusions suffer from significant energy loss between the energy source at the proximal end of the catheter and the driller located at the distal end of the catheter, as well as limited working life due to material fatigue. For example, with an ultrasound catheter, the ultrasonic energy usually originates from an ultrasound transducer at the proximal end of the catheter and is then transmitted to the distal head of the catheter as a sinusoidal wave, causing the distal head to vibrate and either ablate or disrupt the target occlusion.

To reach treatment sites, such catheters must be rather long—about 90-150 cm or more—and therefore a large amount of energy must initially be transmitted to reach the distal end. At the same time, to be flexible enough to course through highly tortuous vessels, the catheter must be reasonably thin. The long length and narrow diameter combine to make wire breakage a common problem due to the stress and wear from the high energy pulses. Guide wires stiff enough to penetrate hard occlusions have the disadvantage that their inflexibility and straight tips make navigating through tortuous vessels difficult and increase the risk of vessel perforation. Rigid materials that are sufficiently flexible to accommodate the highly tortuous vessels have the problem of buckling, due to the proximal location of the pushing source. Buckling results in energy loss by transfer to transverse forces and friction against the lumen housing the rigid material. All such devices provide limited success rate ranging from 40-70%.

Occlusions comprise a variety of materials of different density and hardness. Therefore, the nature of the energy used in a re-canalization device should suit the specific occlusion and the penetration should be controlled to prevent perforation of the artery walls or damage to healthy tissue. Additionally, because the energy originates at the proximal end of the catheter it must be able to reach the distal end of the device near the occlusion at a level sufficient to effect penetration of the occlusion without damaging the conductive wires and without sacrificing flexibility of the device. As previously described, current devices suffer either from an insufficient amount of energy transferred to the distal end of the device or a mismatch between the type of energy delivered and the type of occlusion, sometimes resulting in too much force being applied and thereby increasing the risk of damage, or even perforation, of the lumen wall. Accordingly, there is a need for a system or apparatus that can transfer adequate energy to the re-canalization device.

Guide wires are used for navigation within blood vessels, guiding various catheters through blood vessels, and for specific applications such as re-canalization of partial or full occlusions of blood vessels. The guide wires widely used in interventional cardiology and radiology (peripheral and cardiovascular) generally have a variety of diameters (e.g., 0.014 inches, 0.018 inches, 0.035 inches). These small diameters limit the force that may be applied and transferred to the tip of the guide wire for such purposes (typically several grams to about 15 grams for stiff wires) and also limit the control available for actively directing the guide wire through obstacles, for example to cross a vessel occlusion.

Therefore, there is a need for an apparatus for penetrating vessel occlusions comprising a guide wire that allows a greater force to be applied at the distal end of a guide wire for penetrating a partial or full occlusion, as well as a device that assists traversing obstacles or tortuous elements within blood vessels with a guide wire. There also is a need in the art for an apparatus for penetrating vessel occlusions comprising a guide wire that avoids the problem of energy transfer from the proximal to distal end of the catheter and that improves the usefulness of a stiff guide wire as the structure for penetrating a vessel occlusion.

SUMMARY OF THE INVENTION

It is an object of the invention to provide an apparatus for penetrating a vessel occlusion that is able to reversibly attach or couple a guide wire to catheter to enhance the force that may be applied to penetrate a vessel occlusion using the distal tip of the guide wire. It is a further object of the invention to couple a guide wire to a catheter using friction forces applied to the guide wire to enhance control of the guide wire for penetrating a vessel occlusion.

The present invention is directed to an apparatus for penetrating a vessel occlusion, where the apparatus has a guide wire and a mechanism for attaching or coupling the guide wire to the catheter, preferably the distal end of the catheter and preferably during distal vibration. The guide wire is attached to the catheter by friction forces between the guide wire and a guide wire attachment lumen generated in broad terms by movement of the catheter and in specific terms by the particular embodiment of the attachment mechanism that utilizes this principle. The catheter may be a passive catheter or an active catheter. By "passive catheter" is meant a standard endovascular catheter that may be used for current stiff wire re-canalization procedures. By "active catheter" is meant a catheter that has a mechanism for generating a vibration at the distal end of the catheter for penetrating an occlusion. Coupling the guide wire to the passive catheter in accordance with the invention permits use of the catheter, which inherently has better push-ability than the guide wire, to push or pull the distal end of the guide wire, to significantly enhance the axial force that may be applied to the guide wire to penetrate a vessel occlusion. Moreover, when the attachment mechanism of the invention is used with an active catheter, the vibrational motion generated in the catheter may be transferred to the guide wire in conjunction with the increased axial force, to further enhance the occlusion penetrating capabilities of the guide wire. The attachment lumen may be a portion of the guide lumen or it may be a specially designed lumen through which the guide wire passes.

The guide wire attachment mechanism of the invention attaches the guide wire to the catheter based on movement of the portion of the catheter where the attachment mechanism is located, for example by acceleration force, by a particular direction of movement of the portion of the catheter, or by movement of a specially designed lumen through which the guide wire passes. The motion or acceleration generates frictional forces against the guide wire by the wall of the attachment lumen surrounding the guide wire that couples the guide wire to the catheter. The frictional forces are created by the guide wire being pressed up against the wall of an attachment lumen by a piston, or by the guide wire being bent relative to the attachment lumen. As the coupling is force-limited and the force is reduced in the absence of a vibration force or in the absence of movement of the catheter cap, the operator can used the guide wire in a standard manner as well.

An advantage of the present invention is that by attaching the guide wire to the catheter in a reversible—that is force-specific—manner, and in particular when attachment of the guide wire is at the distal end of the catheter, the force that may be applied against the occlusion using a guide wire may be greater than that possible using a stiff guide wire and a standard catheter without the attachment mechanism. Further, control over the guide wire tip during occlusion penetration is improved, because the guide wire may be locked in the catheter. Still further, when used in conjunction with an apparatus that generates a vibration in the distal tip of the catheter, the attachment mechanism of the invention permits transfer of the vibration motion to the guide wire in addition to the increased force that may be applied to the guide wire to penetrate the occlusion.

DESCRIPTION OF DRAWINGS

FIG. 1A depicts in a cut-away view the locking of a guide wire upon forward acceleration, and FIG. 1B depicts in a cut-away view the locking of a guide wire upon backward acceleration.

FIG. 5A depicts an embodiment in which the attachment lumen is parallel to the longitudinal axis of the catheter cap; FIG. 5B depicts an embodiment in which the attachment lumen is set at an angle relative to the longitudinal axis of the catheter cap.

FIG. 6A depicts an embodiment in which the attachment lumen is parallel to the longitudinal axis of the catheter cap; FIG. 6B depicts an embodiment in which the attachment lumen is set at an angle relative to the longitudinal axis of the catheter cap.

DETAILED DESCRIPTION OF THE INVENTION

Figure 1A:
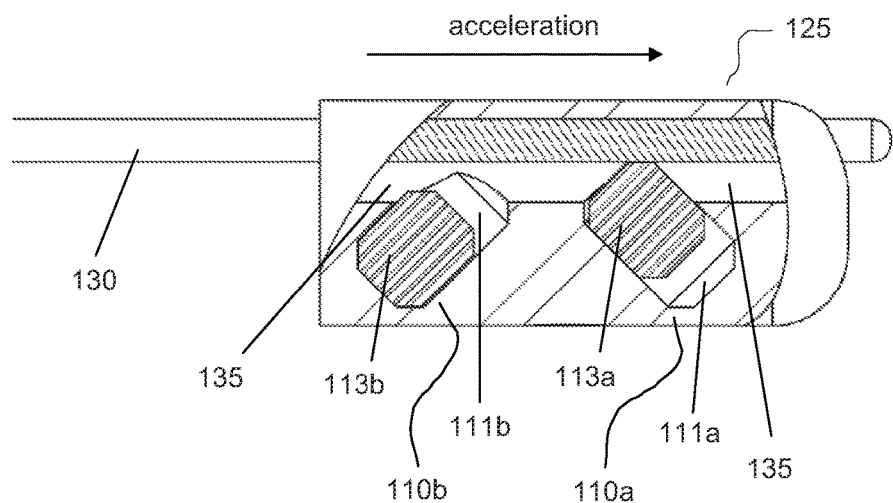
FIGS. 1A-B illustrate the operation of an embodiment of the apparatus of invention comprising acceleration pistons.

The present invention provides an apparatus and method for improved guide wire-based re-canalization of a partial or total occlusion in a blood vessel. The apparatus of the invention may also be applicable to clearing occlusions from other body lumens. Specifically, the apparatus of the invention comprises a catheter having a proximal end and a distal end; a guide wire; and a guide wire attachment mechanism. In some embodiments, the apparatus may further comprise a vibration-generating member, said vibration-generating member operably connected to said guide wire via said guide wire locking mechanism and an external vibrational energy source operably attached to the vibration-generating member.

The guide wire attachment mechanism of the invention generates frictional forces on the guide wire against an attachment lumen in a defined portion of the catheter. The frictional forces are generated when the portion of the guide wire containing the attachment mechanism moves relative to the guide wire, which causes contact with the guide wire which in turn contacts the wall of the attachment lumen. Accordingly, the attachment is force-dependent. The force-dependent attachment or clamping of the guide wire to the catheter is also referred to herein as partial attachment, by which is meant that the guide wire may be either freely moving within the catheter or attached to the catheter depending on the movement of that portion of the catheter. For example, operator may pull or push the guide wire freely within the catheter, while at the same time the guide wire can—at some power limit (e.g., about 0.01-1 Newton force)—be attached to and move with the catheter via the attachment mechanism of the invention. The attachment mechanism may be located within a defined portion of the catheter at some distance from the distal tip of the catheter, but preferably is in the distal region of the catheter to improve guide wire support (e.g., 1-20 mm from the distal tip of the catheter), for example in a catheter cap, as this is a more efficient arrangement.

In one embodiment, the guide wire may be attached to the catheter by frictional forces generated when a structure in the catheter cap that comprises accelerator pistons accelerates relative to the guide wire. Forward acceleration of the catheter cap causes a piston to engage the guide wire by pressing it up against the attachment lumen wall thereby clamping the guide wire to the catheter. Acceleration of the catheter cap in the reverse direction causes another piston to engage the guide wire by pressing it up against the wall of the attachment lumen.

In another embodiment, the guide wire may be attached to the catheter by frictional forces generated by movement of the guide wire in one direction relative to the catheter. In this embodiment a spring-based piston presses against the guide wire, but at an angle such that the guide wire may more easily be, e.g., pushed in the distal direction (or pulled in the proximal direction) than moved in the opposite direction.

In yet another embodiment, the guide wire may be attached to the catheter by frictional forces generated against the guide wire as it passes through a specially designed lumen. This embodiment takes advantage of the frictional forces that a lumen wall may exert against a bent guide wire.

In still another embodiment, the guide wire may be attached to the catheter by frictional forces generated at least in part by a high friction surface against the guide wire as it passes through the attachment lumen of the catheter cap.

In a further embodiment, the guide wire may be attached to the catheter by frictional forces against the guide wire as it passes through the catheter cap lumen, where the frictional forces are generated at least in part by changes in the diameter of attachment lumen as the catheter cap is oscillated.

The aforementioned embodiments, as well as other embodiments, delivery methods, different designs and variations of the guide wire attachment mechanism of the invention are discussed and explained below with reference to the accompanying drawings. Note that the drawings are provided as an exemplary understanding of the present invention and to schematically illustrate particular embodiments of the present invention. The skilled person will readily recognize other similar examples equally within the scope of the invention. The drawings are not intended to limit the scope of the present invention defined in the appended claims.

Figure 1B:
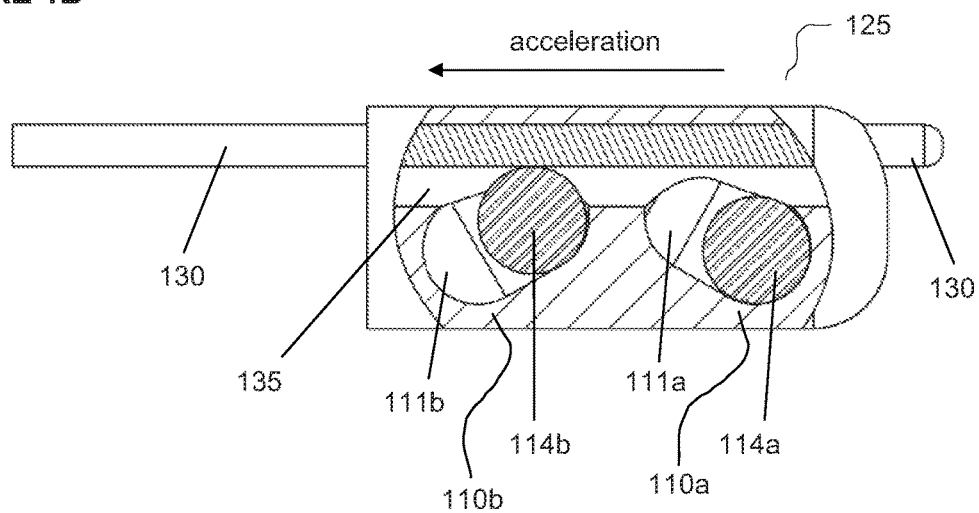

One embodiment of the guide wire attachment means is depicted in FIGS. 1A-1B. In this embodiment, a portion of the catheter contains acceleration pistons 110a, 110b that may comprise a cylinder 113a, 113b or a ball 114a, 114b that is capable of moving freely through a slot 111a, 111b towards a guide wire attachment lumen 135 to push a guide wire towards the wall of the attachment lumen. A piston may be designed to move in a preferred direction—either in the forward direction (i.e., distally, toward the distal tip 121 of the catheter) or the backward direction (i.e., proximally), based on the angle of the piston. In the embodiment depicted in FIGS. 1A and 1B, the preferred direction for acceleration piston 110a is distally and the preferred direction for acceleration piston 110b is proximally, as indicated by the arrows. The portion of the catheter containing the acceleration pistons 110a, 110b may be anywhere along the catheter, but preferably, it is at the distal end of the catheter (not shown) in a catheter cap 125. As illustrated in FIG. 1A, the acceleration piston 110a may comprise a slot 111a through which the cylinder 113a (or ball 114a, not shown) may slide into the attachment lumen 135 toward the guide wire 130 upon forward (distal) acceleration of the catheter cap 125 (as shown by the arrow), creating a friction force that couples the guide wire 130 to the catheter cap 125. During distal acceleration, the cylinder 113b (or ball 114b, not shown) of the acceleration piston 110b having a preferred proximal direction response, remains in the slot 111b away from the guide wire 130. Similarly, as illustrated in FIG. 1B, the acceleration piston 110b may comprise a slot 111b through which the ball 114b (or cylinder 113b, not shown) may slide into the attachment lumen 135 toward the guide wire 130 upon backward (proximal) acceleration of the catheter cap 125 (as shown by the arrow), creating a friction force that couples the guide wire 130 to the catheter cap 125. During proximal acceleration, the ball 114a (or cylinder 113a, not shown) of the acceleration piston 110a having a preferred distal direction response remains in the slot 111a away from the guide wire 130. The embodiments illustrated in FIGS. 1A and 1B depicts two acceleration pistons 110a, 110b, however the catheter cap 125 may comprise more than two acceleration pistons for a firmer hold on the guide wire 130. Alternatively, the catheter cap may comprise one acceleration piston that is butterfly shaped (not shown), which may rotate up into the attachment lumen to lock the guide wire upon acceleration of the catheter cap in either direction.

Figure 2:
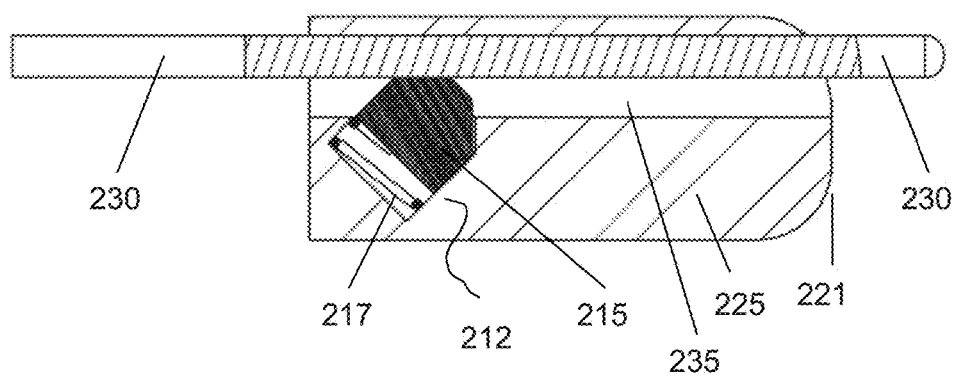
FIG. 2 illustrates in cross-section an embodiment of the apparatus of the invention in which a spring piston may be positioned to favor attachment of the guide wire based on movement of the guide wire in one direction over another.

In another embodiment of a guide wire attachment mechanism, which is illustrated in FIG. 2, a portion of the catheter comprises a spring piston 212 for attaching a guide wire 230 to the catheter (not shown) by friction forces against an attachment lumen 235. Preferably this portion of the catheter is a catheter cap 225 at the distal end of the catheter, as shown in FIG. 2, but the portion may be anywhere in the catheter. The spring piston 212 is a piston comprising a spring 217 and it provides a constant pressure against the guide wire 230, but may press the guide wire 230 more firmly against the wall of the attachment lumen 235 when the guide wire 230 moves in a favored direction relative to the catheter compared when the guide wire 230 moves in the opposite (disfavored) direction. The attachment lumen 235 may be straight, as illustrated in FIG. 2, however in alternative embodiments it may comprise a curve, as shown for example as lumen 336 in FIG. 3. Combinations of the elements of attachment mechanisms depicted in FIGS. 1-4 and as described herein are within the skill in the art and encompassed by the invention.

Increased pressure in the favored direction may be effected by the position of the spring piston 212 and the shape of its contact area 215. Thus, in the embodiment depicted in FIG. 2, the spring piston 212 is designed to favor allowing forward (distal) movement of the guide wire 230 over backward (proximal) movement relative to the catheter, because the spring piston 212 and its contact area 215 are angled toward the distal tip 221 of the catheter. An embodiment favoring backward movement of the guide wire 230 relative to the catheter could be achieved by angling the spring piston 212 in the opposite direction, using the same shaped piston contact area 215 in this embodiment. In some embodiments it may be desirable to have a neutral effect on direction of guide wire 230, in which case the spring piston 212 maybe oriented orthogonal to the guide wire 230 and the longitudinal axis of the attachment lumen 235. The spring 217 in the spring piston 212 may be any type of spring, including helical, leaf spring, membrane etc. to maintain constant pressure by the contact area 215 of the spring piston 212 against the guide wire 230. In this embodiment, the guide wire 230 is attached to the catheter cap 225 up to the force generated by the friction against the wall of the attachment lumen 235. The surface between the piston contact area 215 and the guide wire 230 and the surface between the guide wire 230 and the attachment lumen 235 can be designed to have either a low friction coefficient or a high friction coefficient, depending on the needs of the procedure.

Figure 3:
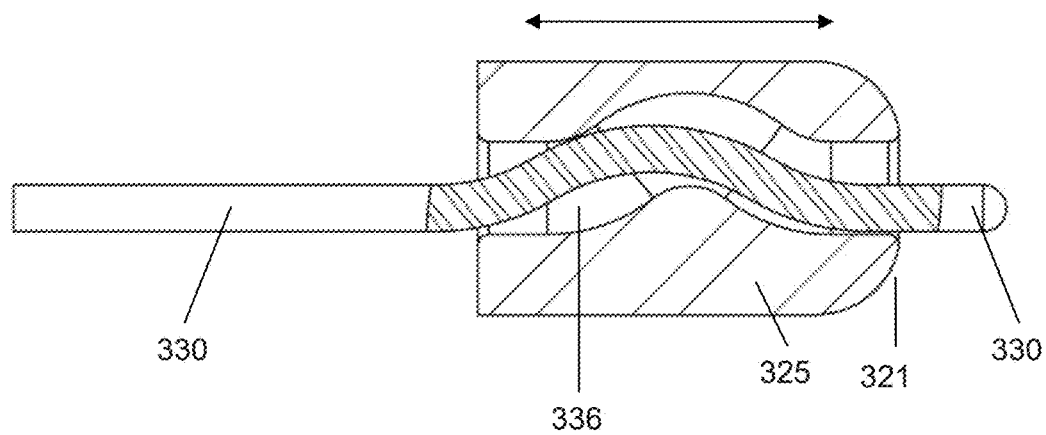
FIG. 3 illustrates in cross-section an embodiment of the guide wire attachment mechanism in which a attachment lumen has a curve so as to bend the guide wire and create sufficient friction at certain forces to effectively attach the guide wire to the catheter.

In yet another embodiment of the guide wire attachment mechanism, illustrated in FIG. 3, the friction to hold the guide wire 330 is generated by an attachment lumen having a curved path, referred to herein as a curved attachment lumen 336. In this embodiment, a portion of the catheter comprises a curved attachment lumen 335 for bending the guide wire to generate friction forces against the guide wire (as discussed above) for attaching the guide wire 330 to the catheter. Preferably this portion of the catheter is a catheter cap 325 at the distal tip 321 of the catheter. This embodiment has two modes. In a first mode, the catheter cap 325 is stationary and the operator may push or pull the guide wire through 330 the catheter at will. Friction against the guide wire 330 is slightly higher than in catheters having a standard straight attachment lumen. In a second mode, where the catheter cap 325 accelerates, friction is generated between the guide wire 330 and the curved attachment lumen 336, causing the guide wire 330 to be attached to the catheter cap 325, and thus the catheter. Specifically, when the catheter cap 325 moves, whether by the operator or by oscillation in an active catheter (not shown), the guide wire 330 is clamped to the catheter cap 325 by the frictional forces generated against the guide wire 330 by the wall of the curved attachment lumen 336, and the guide wire 330 moves with the catheter cap 325.

The embodiments of the a guide wire attachment means depicted in FIGS. 1-3 may be used with a standard catheter, which effects coupling of the guide wire to the catheter cap when the catheter is moved in the axial direction. However, the embodiments are also useful in conjunction with active catheters, where energy is inputted from the proximal end of the catheter to generate oscillations at the distal end of the catheter. In particular, to overcome additional limitations of the prior art—specifically the loss of mechanical energy transfer from the proximal end to the distal end of the catheter, the apparatus of the invention is particularly useful in conjunction with active catheters having vibration-generating means for generating a vibration at the distal end of the catheter, in a particular a vibration-generating means for generating axial oscillation of a vibration member at the distal end of the catheter.

Thus, the guide wire attachment mechanism of the invention may be used with standard passive catheters, that is standard endovascular catheters used for stiff guide wire penetration procedures. Alternatively the attachment mechanism of the invention may be used with active catheters, such as catheters having vibration-generating means at the distal end of the catheter for penetrating a vessel occlusion, in particular active catheters having vibration systems designed for efficiently transferring vibration energy to the distal end of the catheter. It is noted that when used with an active catheter, the guide wire penetration procedure used in conjunction with the present invention may be implemented alternately with the vibrating member and occlusion impact element of the active catheter, as the guide wire is usually pulled inside the catheter during operation of such an active catheter. Alternatively, an active catheter may be designed such that vibration generating means may both couple the guide wire to the catheter and vibrate the guide wire, by oscillating a section of the catheter containing the guide wire attachment mechanism. Where the guide wire acts as a hammer on the occlusion, it preferably extends from about 0.1 mm to about 5 mm beyond the catheter cap.

The present invention is particularly useful with the active catheter comprising a pulling member-spring element combination as described in detail in co-pending U.S. application Ser. No. 13/022,710 (recanalization), based on U.S. provisional application No. 61/302,669, entitled "Device for Recanalization of Vessel Occlusions and Method of Use", filed on date even herewith. The pulling member-spring element apparatus generates a vibration force that oscillates the vibratable member by a pulling force rather than pushing or combined pulling-pushing force, and is less sensitive to unpredictable geometry such as the sometimes tortuous curvature of blood vessels than PCI devices that use pushing forces. In particular, the apparatus of co-pending U.S. application Ser. No. 13/022,710 (recanalization) comprises a spring element, a pulling member, a vibratable member, all housed in a catheter, and an external vibrational energy source operably connected to the pulling member. At the distal tip of the apparatus is a vibratable member, which may be, for example, a cap—similar a catheter cap, or a cap shaped to increase mechanical impact and improve penetration. The vibratable member oscillates in response to the pulling force of the pulling member and the return force from the spring element. The oscillation or vibration of the vibratable member can effect penetration of the occlusion. Specifically, the vibrational energy source is adapted to repeatedly pull and release the pulling member so as to vibrate the vibratable member via the spring element. The pulling member is capable of simultaneously compressing the spring element in the proximal direction and therefore transferring energy to the vibratable member. The spring element is capable of converting the stored energy to kinetic energy locally (upon release of the pulling member tension), thereby moving the vibratable member in the distal direction. The acceleration of the kinetic energy carries the expansion of the spring element to extend the distal end of the spring element beyond the no load (resting) position, thereby pushing the vibratable member further distally. In a blood vessel having an occlusion, the kinetic energy is transferred from the vibratable member to impact the occlusion. The vibratable member, located at the distal tip of the catheter, is thereby made oscillate at a frequency and amplitude sufficient to penetrate an occlusion in a body lumen. When used with the present invention, the catheter may be a conventional interventional medical catheter having a lumen to accommodate the pulling member and also a lumen to accommodate a guide wire and the guide wire attachment mechanism of the present invention, as well as other elements such as for steering, motion measurement element, to infuse contrast material, or to remove occlusion debris from the drilling area.

The present invention is also particularly useful with the active catheter comprising a hydraulic lumen as described in detail in co-pending published U.S. application no. US 2009/0292296A1, entitled "Method and Device for Recanalization of Total Occlusions". The hydraulic mechanism transfers hydraulic pulses to the distal end of the catheter to expand and contract a distal element thereby oscillating a vibratable member at the distal end of the catheter with minimal loss of energy transfer. Briefly, the vibration-generating means described in US 2009/0292296A1 includes a hydraulic catheter comprising a catheter head and at least one hydraulic lumen operably connected to vibrational energy source to input energy pulses, preferably hydraulic pressure waves or pulses, into the at least one hydraulic lumen of the hydraulic catheter for generating a vibration force at the distal end of the catheter for oscillating a vibration member. The hydraulic lumen is capable of efficiently transferring energy to a vibratable member at its distal tip to oscillate that vibratable member to penetrate an occlusion in a body lumen. The hydraulic lumen is a sealed structure containing a liquid, preferably a biologically compatible liquid, and having a proximal end and a distal end. The hydraulic lumen preferably comprises a proximal element, a distal element and a hydraulic tube connecting the proximal element to the distal element.

Still referring to US 2009/0292296A1, the vibrational energy source is external of the catheter, but is operably connected thereto, in particular to the hydraulic lumen of the hydraulic catheter. Preferably, the vibrational energy source is capable of generating at least one of hydraulic pressure wave, comprising at least one frequency and at least one amplitude, into the hydraulic lumen preferably via the proximal element of the hydraulic lumen. The proximal element may mediate initiating the hydraulic pressure wave through the hydraulic tube preferably by being mechanically compressed or shaken in the proximal direction. The hydraulic tube transmits the hydraulic pressure wave to the distal element. The distal element may be a vibratable member or may effect oscillation of a vibratable member, which vibration is driven by the hydraulic pressure wave. The distal element may be made to vibrate or oscillate by pushing liquid into it, thereby expanding it, and then removing the pressure, thereby allowing it to "spring back". The distal element may be, for example, an active bellows, an elastic membrane or a spring that is sealingly covered in an expansible or compliant material. The catheter head, which is the distal-most region of the hydraulic catheter, comprises the distal element. The proximal and distal elements, but not the hydraulic tube, may be made to expand and contract. Within the catheter head, the distal element of the hydraulic lumen cooperates with the hydraulic pressure waves to generate a vibration force useful for penetrating a vessel occlusion.

Further referring to US 2009/0292296A1, the catheter head comprises three functional components: a vibratable member, a return force component and an occlusion impact element. The vibratable member oscillates in response to the distally directed force from the hydraulic pressure waves and the proximally-directed force of the return force component. The vibration motion of the vibratable member is transferred to the occlusion impact element, which effects penetration of the occlusion. These three functional components may comprise one or more structures. For example: the distal element of the hydraulic lumen may be a structure that performs all three functions; the distal element of the hydraulic lumen may transmit a vibration energy and return force to a separate structure that is a vibratable member and occlusion impact element; or a structure (or combination of structures) separate from the distal element of the hydraulic lumen may comprise all three functional components. Preferably, the three functional components are built into the distal element of the hydraulic lumen.

The present invention is not recommended for use with the embodiment of the hydraulic catheter that involves vibrating the guide wire. In any event, it should be noted that the frictional forces used to attach the guide wire in the present invention differ markedly from the guide wire anchor of US2009/0292296A1, in that the forces are entirely passive and internal to the device, operating as a function of movement of the guide wire or catheter. By contrast, the guide wire anchor mechanism of US2009/0292296A1 relies on externally applied forces, such as inflation media pumped into inflation balloons, to stabilize the guide wire during implementation of the vibration force. Indeed, the two mechanisms are not interchangeable.

For both co-pending U.S. application Ser. No. 13/022,710 (recanalization) and US 2009/0292296A1 the vibrational energy source is external of the catheter, but is operably connected to the vibration-generating member. The vibrational energy source may be any energy source that is capable of generating at least one vibratory energy pulse comprising at least on frequency and at least one amplitude. The vibrational energy source may be, for example, a motor, a shaker, a piezoelectric motor or an actuator.

Figure 4:
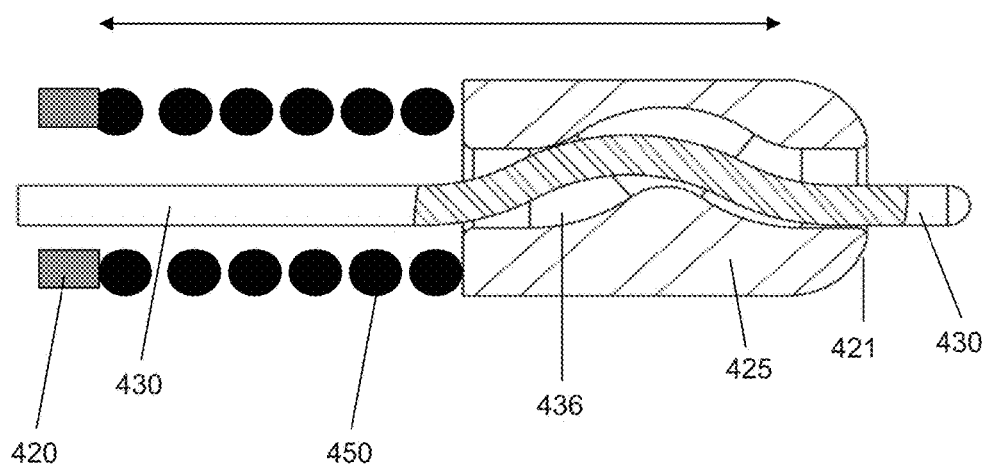
FIG. 4 illustrates in cross-section the embodiment of FIG. 3 used in conjunction with an active catheter comprising a vibration-generating means.

The guide wire attachment mechanism may used in conjunction with an active catheter having a vibration-generating means, such as the pulling member-spring element described in co-pending U.S. application Ser. No. 13/022,710 (recanalization), as illustrated in FIG. 4, or the hydraulic system described in published U.S. application no. US 2009/0292296A1 which comprises, e.g., a distal bellows. Elements that are not spring-like structures but that generate an oscillation, preferably an axial oscillation, at the distal end of the catheter are also within the scope of this combination embodiment represented by FIG. 4. Thus, for example an elastic membrane as described in US 2009/0292296A1, or piezomotors as described in the art, or comparable vibration-generating means, are equally contemplated components of a vibration-generating means within the meaning of the present invention. One example of such a combination is illustrated in FIG. 4, which demonstrates how the guide wire attachment mechanism depicted in FIG. 3 may be used in conjunction with an active catheter comprising a vibration-generating means. In particular, FIG. 4 depicts a schematic cross-section through a catheter cap 425 comprising the curved attachment lumen 436 embodiment shown in FIG. 3 attached to the distal end of an exemplary spring 450 of a vibration-generating means to impart axial vibration to the guide wire 430 via the curved attachment lumen 436 in the catheter cap 425. For clarity of illustration in FIG. 4, the vibration-generating means is depicted as a spring 450, which represents a means by which the catheter cap 425 may be oscillated in an axial direction. Other combinations of a guide wire attachment mechanism, such as those illustrated in FIGS. 1 and 2, and an active catheter (having a vibration-generating means) are within the scope of the invention, as the principle of the oscillating catheter cap effecting movement to generate friction is the same.

Figure 5A:
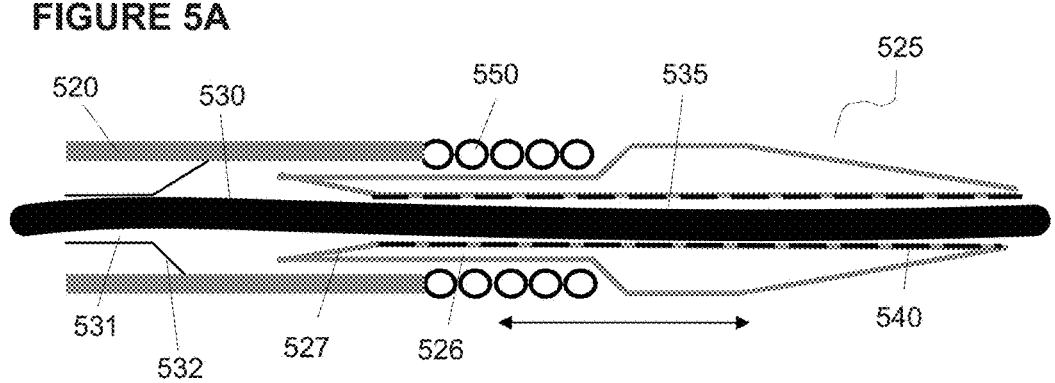
FIGS. 5A and 5B illustrate in cross-section embodiments of the guide wire attachment mechanism in which the attachment lumen has a frictional surface that includes a high friction flexible polymer.
Figure 5B:
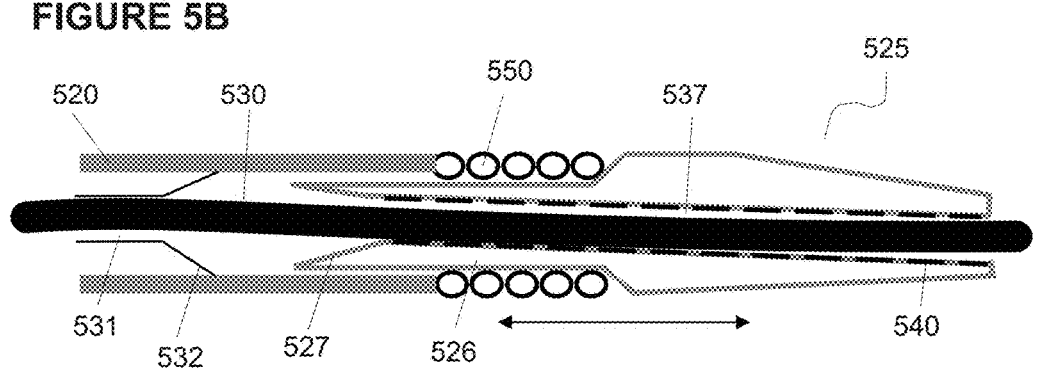

In the embodiments depicted in FIGS. 5A and 5B, a high friction surface 540 within the catheter cap 525 provides friction against guide wire 530 as the catheter cap 525 moves relative to the guide wire 530. In the embodiment depicted in FIG. 5A, the catheter cap 525 has a straight attachment lumen 535 that lies parallel to the longitudinal axis of the catheter cap 525 and has a diameter slightly larger than the diameter of the guide wire 530. FIG. 5B illustrates a similar embodiment, differing from the embodiment of FIG. 5A only in that the catheter cap 525 has a tilted or angled attachment lumen 537. The attachment lumen 537 of FIG. 5B is set at angle relative to the longitudinal axis of the catheter cap 525. The attachment lumen 535, 537 has a high friction surface 540 that includes a high friction flexible polymeric material. The high friction surface 540 may be the surface of the attachment lumen 535, 537 itself where the catheter cap 525 is manufactured from a relatively high friction material, or the high friction surface 540 may be a coating on the attachment lumen 535, 537. Suitable materials for the high friction surface 540 include low durometer thermoplastic polymers, such as, for example, a polyether block amide (e.g., PEBAX) or a polyurethane. The catheter cap 525 may be manufactured from metal, plastic or other bio-compatible material.

Preferably, the catheter cap 525 is used in conjunction with an active catheter having a vibration-generating means, such as the pulling member-spring element described in co-pending U.S. application Ser. No. 13/022,710 (recanalization), filed on date even herewith. Thus, as shown in FIGS. 5A and 5B, the catheter cap 525 may be attached to the distal end of a compression spring 550. The proximal end of the compression spring 550 may be attached to the catheter 220. As shown in FIGS. 5A and 5B, the catheter cap 525 may optionally have a proximal portion 526 that extends through the compression spring 550, which provides axial alignment relative to the compression spring 550. The proximal-most portion of the lumen of the catheter cap 525 may flare out to form a funnel-like shape 527 to direct the guide wire 530 when it is pushed by the operator between the guide wire lumen 531 and catheter cap 525. The distal-most portion of the guide wire lumen 531 may be similarly flared 532.

Figure 6A:
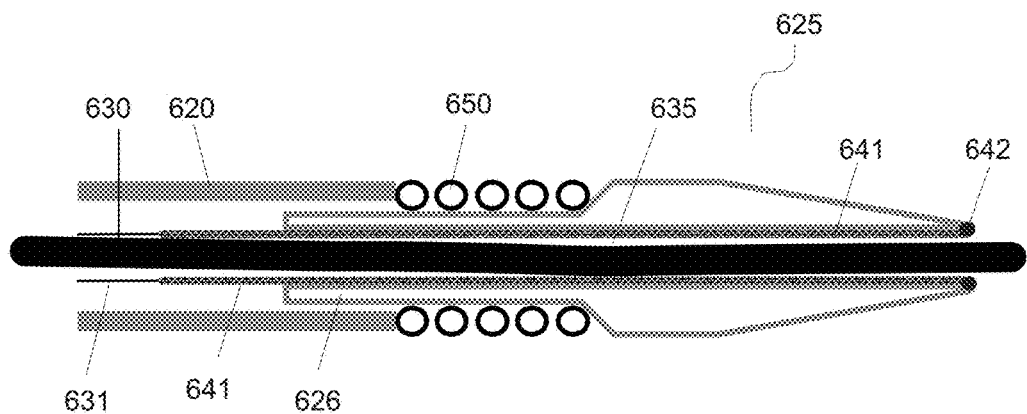
FIGS. 6A and 6B illustrate in cross-section an embodiment of the guide wire attachment mechanism in which the attachment lumen has a frictional surface that includes a flexible tube.
Figure 6B:
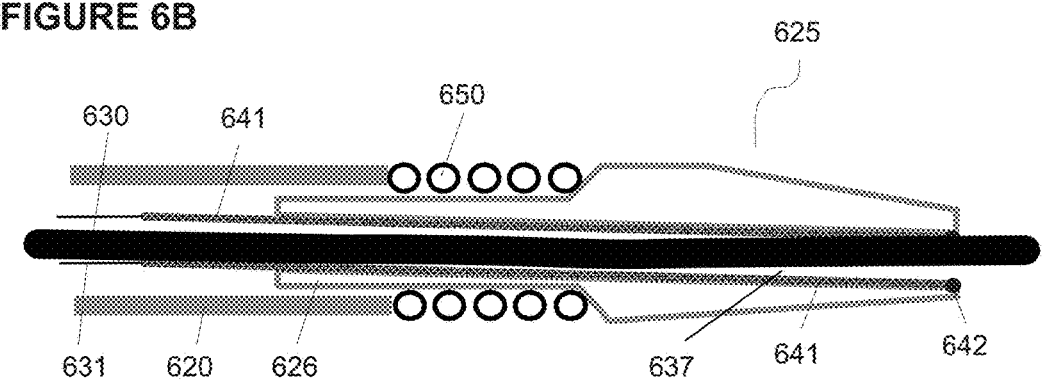

In another embodiment of the guide wire attachment mechanism, the attachment lumen 635 of the catheter cap 625 may include a flexible tube 641, as illustrated in FIGS. 6A and 6B. The flexible tube 641 may provide a high friction surface to generate frictional forces against the guide wire 630 as the catheter cap 625 moves relative to the guide wire 630. The flexible tube 641 preferably is longitudinally flexible and stretchable along its axis. By longitudinally flexible is meant that the flexible tube 641 may bend along the longitudinal axis. Suitable materials for the flexible tube 641 include, for example, a polyether block amide such as PEBAX, having a durometer of about 25; a polyurethane, such as Pellethane 80A; or similar materials.

In the embodiment depicted in FIG. 6A, the catheter cap 625 has a straight attachment lumen 635 that lies parallel to the longitudinal axis of the catheter cap 625 and has a diameter slightly larger than the diameter of the guide wire 630. FIG. 6B illustrates a similar embodiment, differing from the embodiment of FIG. 6A only in that the catheter cap 625 has a tilted or angled attachment lumen 637. The attachment lumen 637 is set at slight angle relative to the longitudinal axis of the catheter cap 625. The tilted or angled attachment lumen in embodiments of FIGS. 5B and 6B may serve two purposes. First, the angled attachment lumen 537, 637 may contribute to the frictional forces against the guide wire 530, 630, as the operator pushes the catheter more forcefully. For example, the angle between the direction of motion and the guide wire may generate lateral friction forces on the guide wire 530, 630, causing it to vibrate with the catheter cap. Second, the angled attachment lumen 537, 637 may assist in maneuvering the guide wire; for example, the catheter may be rotated to aim the guide wire in a particular direction—when used to penetrate an occlusion.

Preferably, the catheter cap 625 of the embodiments of FIGS. 6A and 6B is used in conjunction with an active catheter having a vibration-generating means, such as the pulling member-spring element described in co-pending U.S. application Ser. No. 13/022,710 (recanalization), filed on date even herewith. Thus, as shown in FIGS. 6A and 6B, the catheter cap 625 may be attached to the distal end of a compression spring 550. The proximal end of the compression spring 550 may be attached to the catheter 220. As shown in FIGS. 6A and 6B, the catheter cap 625 may optionally have a proximal portion 626 that extends through the compression spring 650, which provides axial alignment relative to the compression spring 650. The flexible tube 641 may be attached at its distal end 642 to the distal tip of the catheter cap 625, extends through the attachment lumen 635, 637, and may be attached at is proximal end to a portion of the catheter. As shown in the embodiments of FIGS. 6A and 6B, the flexible tube 641 may extend beyond the proximal portion 626 of the catheter cap 625, and be attached at its proximal end to the distal end of the guide wire lumen 631. Where the flexible tube 641 is used in an active catheter as shown in FIGS. 6A and 6B, in addition to providing friction against the guide wire 630, the flexible tube 641 may change its inner diameter as the compression spring 650, or other vibration-generating means, contracts or expands, thereby effectively changing the attachment lumen diameter and the probability that the guide wire 630 will encounter frictional surface.

The inner diameter of the flexible tube 641 changes as the compression spring compresses or expands. Specifically, when the compression spring 650 is in a compressed state, the flexible tube 641 has a smaller inner diameter due to wrinkling inward and increased contact with the guide wire 630, thereby increasing the friction generated against the guide wire 630. The wrinkling (or collapsing inward) of the flexible tube 641 when the compression spring 650 is compressed may occur because the flexible tube 641 is bounded from the outside by the inner wall of the catheter cap 625. Extension of the compression spring 650, expands the flexible tube 641 and also provides a smaller inner diameter, thereby increasing the friction generated against the guide wire 630. By comparison, when the compression spring 650 is in a relaxed state, it provides less friction against the guide wire 630 than when the flexible tube 641 is contracted or extended.

Thus, the apparatus of the invention may comprise the following. An apparatus for penetrating a vessel occlusion, comprising: a catheter; a guide wire; a guide wire attachment mechanism located within a portion of said catheter; wherein said guide wire attachment mechanism is capable of generating friction forces on said guide wire upon movement of said portion of said catheter relative to said guide wire to couple said guide wire to said catheter. In one embodiment, said portion of said catheter is a catheter cap located at a distal end of said catheter. In one embodiment, said attachment mechanism comprises an attachment lumen and two or more acceleration pistons. In another embodiment, said attachment mechanism comprises an attachment lumen and a spring piston. In yet another embodiment said attachment mechanism comprises a curved attachment lumen. In still another embodiment, said attachment mechanism comprises an attachment lumen having a high friction surface comprising a flexible polymer. In one aspect of this embodiment the attachment lumen is set at an angle relative to the longitudinal axis of said catheter cap. In still yet another embodiment, said attachment mechanism comprises an attachment lumen having a flexible tube, said flexible tube comprising a smaller diameter upon contraction and a larger diameter upon extension compared to a relaxed state. In one aspect of this embodiment the attachment lumen is set at an angle relative to the longitudinal axis of said catheter cap.

In one embodiment, the apparatus may further comprise a vibration-generating member, said vibration-generating member operably connected to said guide wire via said guide wire attachment mechanism; and a vibrational energy source operably connected to said vibration-generating member, wherein said vibrational energy source is adapted to generate at least one oscillation at a distal end of said catheter via said vibration-generating member. In one aspect of this embodiment said vibration-generating member is selected from the group consisting of: a spring element and a pulling member; a hydraulic lumen and a distal bellows; a hydraulic lumen and an elastic membrane; and a piezomotor.

The apparatus may additionally comprise a steering device to assist navigation through an occlusion, especially for use in cases where there are numerous bifurcations near the target occlusion. The catheter may be compatible for use with additional external or internal components that assist visualization of the apparatus or device, and/or to remove drilling debris, for example by suction.

Preferably the catheter has one or more lumens for a guide wire, and one or more lumens for operation of the vibration-generating member. The catheter may also include various lumens for other features, such as a steering wire or other mechanism, contrast materials for visualization, IVUS (intra-vascular ultrasound), elements for measuring distal motion amplitude and force, removal of debris from the occlusion, etc.

The invention additionally encompasses a method of attaching a guide wire to a catheter for use in re-canalization of occluded vessel. The method of coupling a guide wire to a catheter for use in penetrating a vessel occlusion, may comprise: providing a catheter having an attachment mechanism and a guide wire threaded therethrough; and moving said attachment mechanism relative to said guide wire to generate friction forces on said guide wire sufficient to couple said guide wire to said catheter. In one embodiment, said attachment mechanism comprises an attachment lumen and two or more acceleration pistons and said moving step includes accelerating said attachment mechanism relative to said guide wire. In another embodiment, said attachment mechanism comprises an attachment lumen and a spring piston, said spring piston having a shape that favors free movement of said guide wire in a direction at a force, and said moving step includes moving said attachment mechanism in a direction and force unfavorable to free movement of said guide wire. In yet another embodiment, said attachment mechanism comprises a curved attachment lumen, and said moving step includes moving said attachment mechanism so as to generate friction from a wall surface of said curved attachment lumen against said guide wire. In one embodiment, the providing step may further include providing a vibration generating means, wherein the method further comprises: generating a vibration force via said vibration-generating means; said moving step including using said vibration force to generate at least a portion of said friction.

The invention additionally encompasses a method of treating a vessel occlusion. The method may comprise: introducing into a vessel having an occlusion a catheter having an attachment mechanism and a guide wire threaded therethrough; coupling said guide wire to said catheter by moving said attachment mechanism relative to said guide wire to generate friction forces on said guide wire; and penetrating said occlusion using said coupled guide wire. In one embodiment said catheter further includes a vibration-generating means, said method further comprising: generating a vibration force via said vibration-generating means; said coupling step including using said vibration force to generate at least a portion of said friction. In one aspect of this embodiment said vibration force vibrates a vibrating member capable of penetrating said vessel occlusion and said penetrating step includes using said vibration force alternately with said coupled guide wire. The method may further comprise: adjusting periodically the position of said guide wire relative to said catheter so that said guide wire extends from a distal tip of said catheter by a defined amount. Said defined amount may be between about 1 mm-20 mm, or between about 5 mm-15 mm, or between about 5 mm and 10 mm, or between 0.1 mm to about 5 mm.

It will be appreciated by persons having ordinary skill in the art that many variations, additions, modifications, and other applications may be made to what has been particularly shown and described herein by way of embodiments, without departing from the spirit or scope of the invention. Therefore it is intended that scope of the invention, as defined by the claims below, includes all foreseeable variations, additions, modifications or applications.

What is claimed is:

1. An apparatus for coupling a guide wire to a catheter, comprising:
a catheter cap attached to a distal end of a catheter, the catheter cap comprising an attachment lumen extending therethrough and a piston extending out of a wall of said attachment lumen at an oblique angle to a longitudinal axis of said attachment lumen, wherein said catheter cap is configured to reversibly couple to said guide wire.

2. The apparatus of claim 1, wherein said catheter cap is configured to allow movement of the guide wire therethrough in a first direction and inhibit movement of the guide wire therethrough in a second direction opposite the first direction.

3. The apparatus of claim 1, wherein said catheter cap comprises two or more pistons.

4. The apparatus of claim 3, wherein a first one of the pistons extends into said attachment lumen at said oblique angle and wherein a second one of the pistons extends into said attachment lumen at a different oblique angle.

5. The apparatus of claim 1, wherein said piston is spring activated.

6. The apparatus of claim 1, wherein said piston is one of cylindrical and spherical.

7. The apparatus of claim 1, wherein said wall of said attachment lumen comprises a high friction surface comprising a flexible high friction polymer.

8. The apparatus of claim 1, wherein said attachment lumen is linear.

9. The apparatus of claim 1, further comprising:
a vibration-generating element, said vibration-generating element operably connected to said guide wire via said catheter cap; and
a vibrational energy source operably connected to said vibration-generating element, wherein said vibrational energy source is adapted to generate at least one oscillation at a distal end of said catheter via said vibration-generating element.

10. The apparatus of claim 9, wherein said vibrational energy source is selected from the group consisting of: a pulling member, a hydraulic lumen and a piezomotor.

11. The apparatus of claim 9, wherein the vibration-generating element is one of a spring, elastic membrane and an active bellows.

12. A method of coupling a guide wire to a catheter for use in penetrating a vessel occlusion, comprising steps of:
guiding said catheter over said guide wire, said catheter having a catheter cap at a distal end thereof, wherein at a distal end of a vibration generating means, said catheter cap comprising an attachment lumen extending therethrough and a piston extending out of a wall of said attachment lumen at an oblique angle to a longitudinal axis of said attachment lumen; and
moving said catheter cap relative to said guide wire in a first direction to couple said guidewire to said catheter cap.

13. The method of claim 12, further comprising a secondary piston, the method further comprising a step of moving said catheter cap relative to said guide wire in a second direction to couple said guide wire to said catheter cap via said secondary piston.

14. The method according to claim 12, wherein said piston is spring-loaded, said piston configured to permit free movement of said guide wire in said first direction and inhibit movement of said guide wire in a second direction opposite said first direction.

* * * * *